United States Patent
Wojtczuk et al.

(10) Patent No.: US 10,568,514 B2
(45) Date of Patent: Feb. 25, 2020

(54) ENHANCED VISIBLE NEAR-INFRARED PHOTODIODE AND NON-INVASIVE PHYSIOLOGICAL SENSOR

(71) Applicant: MASIMO SEMICONDUCTOR, INC., Irvine, CA (US)

(72) Inventors: Steven J. Wojtczuk, Lexington, MA (US); Xuebing Zhang, Acton, MA (US); William J. MacNeish, III, Newport Beach, CA (US)

(73) Assignee: MASIMO SEMICONDUCTOR, INC., Irvine, CA (US)

( * ) Notice: Subject to any disclaimer, the term of this patent is extended or adjusted under 35 U.S.C. 154(b) by 0 days.

(21) Appl. No.: 16/505,364

(22) Filed: Jul. 8, 2019

(65) Prior Publication Data
US 2020/0000340 A1    Jan. 2, 2020

Related U.S. Application Data

(63) Continuation of application No. 14/858,639, filed on Sep. 18, 2015, now Pat. No. 10,383,520.
(Continued)

(51) Int. Cl.
*A61B 5/00* (2006.01)
*H01L 31/0216* (2014.01)
(Continued)

(52) U.S. Cl.
CPC ...... *A61B 5/0059* (2013.01); *H01L 31/02162* (2013.01); *H01L 31/03046* (2013.01); *H01L 31/105* (2013.01); *A61B 5/6826* (2013.01); *A61B 2562/0238* (2013.01); *Y02E 10/544* (2013.01)

(58) Field of Classification Search
CPC ............... H01L 31/03046; H01L 31/0203
See application file for complete search history.

(56) References Cited

U.S. PATENT DOCUMENTS

| 4,960,128 A | 10/1990 | Gordon et al. |
| 4,964,408 A | 10/1990 | Hink et al. |

(Continued)

OTHER PUBLICATIONS

Standard InGaAs Photodiodes IG17-Series, Laser Components, V2, Aug. 2014, in 11 pages.
(Continued)

*Primary Examiner* — David P Porta
*Assistant Examiner* — Djura Malevic
(74) *Attorney, Agent, or Firm* — Knobbe, Martens, Olson & Bear LLP (57) ABSTRACT

Embodiments of the present disclosure include a photodiode that can detect optical radiation at a broad range of wavelengths. The photodiode can be used as a detector of a non-invasive sensor, which can be used for measuring physiological parameters of a monitored patient. The photodiode can be part of an integrated semiconductor structure that generates a detector signal responsive to optical radiation at both visible and infrared wavelengths incident on the photodiode. The photodiode can include a layer that forms part of an external surface of the photodiode, which is disposed to receive the optical radiation incident on the photodiode and pass the optical radiation to one or more other layers of the photodiode.

20 Claims, 4 Drawing Sheets

Related U.S. Application Data (60) Provisional application No. 62/052,420, filed on Sep. 18, 2014.

(51) Int. Cl.
    *H01L 31/0304*     (2006.01)
    *H01L 31/105*     (2006.01)

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,412,229 A * | 5/1995 | Kuhara ............... G02B 6/4202 257/12 |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,110,758 A * | 8/2000 | Estrera ............... H01J 1/34 438/118 |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |

(56) References Cited

U.S. PATENT DOCUMENTS

| | | |
|---|---|---|
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |

(56) References Cited

U.S. PATENT DOCUMENTS

| | | |
|---|---|---|
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |

(56) References Cited

U.S. PATENT DOCUMENTS

| | | |
|---|---|---|
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,748,307 B2 * | 8/2017 | Cheng .............. H01L 31/02240 |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |

(56) References Cited

U.S. PATENT DOCUMENTS

| | | |
|---|---|---|
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 2003/0070707 A1* | 4/2003 | King ............... H01L 31/02168 136/255 |
| 2003/0145884 A1* | 8/2003 | King ............... H01L 31/02168 136/255 |
| 2006/0161054 A1 | 7/2006 | Reuss et al. |
| 2006/0211922 A1* | 9/2006 | Al-Ali ............... A61B 5/14552 600/310 |
| 2007/0282478 A1 | 12/2007 | Al-Ali et al. |
| 2009/0095926 A1* | 4/2009 | MacNeish, III ... A61B 5/14552 250/505.1 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0181484 A1* | 7/2010 | Inada ............... G02B 5/1876 250/332 |
| 2010/0210930 A1* | 8/2010 | Saylor ............... A61B 5/14532 600/323 |
| 2010/0218819 A1* | 9/2010 | Farmer ............. H01L 31/02167 136/256 |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2011/0291108 A1* | 12/2011 | Shen ............... H01L 31/03687 257/77 |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0262701 A1* | 10/2012 | Said ............... H01L 31/0288 356/4.01 |
| 2012/0283524 A1 | 11/2012 | Kiani et al. |
| 2012/0286328 A1* | 11/2012 | Nishida ............. H01L 27/14649 257/188 |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |

(56) References Cited

U.S. PATENT DOCUMENTS

| | | |
|---|---|---|
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |

OTHER PUBLICATIONS

10Gbps DualBand InGaAs PIN Photodiode, Global Communication Semiconductors, Mar. 2012, in 2 pages.

* cited by examiner

ENHANCED VISIBLE NEAR-INFRARED PHOTODIODE AND NON-INVASIVE PHYSIOLOGICAL SENSOR

RELATED APPLICATIONS

Any and all applications for which a domestic priority claim is identified in the Application Data Sheet of the present application are hereby incorporated by reference under 37 CFR 1.57.

DETAILED DESCRIPTION

I. Introduction

This disclosure in part describes embodiments of non-invasive methods, devices, and systems for measuring a blood analyte, such as oxygen, carbon monoxide, methemoglobin, total hemoglobin, glucose, proteins, lipids, a percentage thereof (for example, saturation) or for measuring many other physiologically relevant patient characteristics. These characteristics can relate, for example, to pulse rate, hydration, trending information and analysis, and the like. In certain embodiments, a non-invasive sensor can interface with tissue at a measurement site, irradiate the tissue, and detect optical radiation after attenuation by the tissue.

This disclosure in part also describes embodiments of a semiconductor device, such as a photodiode, for detecting optical radiation at both visible and near-infrared wavelengths. The semiconductor device can, for example, be used as part of a non-invasive sensor to detect visible and near-infrared wavelengths of optical radiation after attenuation by tissue.

Because individual detectors (for example, individual photodiodes) of non-invasive sensors may be responsive to a limited range of wavelengths of optical radiation, multiple detectors may be used in combination, in some instances, to construct a non-invasive sensor that detects optical radiation at a broad range of wavelengths of optical radiation. For example, it is common to use both an InGaAs photodiode in combination with a Si photodiode in order to measure a broader range of wavelengths. However, each additional detector included in a non-invasive sensor can utilize additional space within the sensor and cause the sensor to be larger or more complicated to assemble. Also, having two sensors at two different positions can affect the optical radiation path length of the respective detected optical radiation of each detector. This inherently introduces inaccuracies and may require, for instance, some post-processing compensation to account for the inaccuracies. Moreover, each additional detector can consume space that may be used in another way, such as to increase the size of one or more other detectors so that a stronger signal may be obtained.

In some embodiments, a photodiode is disclosed herein that can detect optical radiation at a broad range of wavelengths obviating the necessity for two separate photodiodes as was previously utilized. The photodiode can be part of an integrated semiconductor structure that can generate a detector signal responsive to optical radiation at both visible and infrared wavelengths incident on the photodiode. The photodiode can include a window layer that forms part of an external surface of the photodiode. The external surface may be disposed to receive the optical radiation incident on the photodiode and pass the optical radiation to other layers of the photodiode. Advantageously, in certain embodiments, the thickness of the window layer can be minimized or the bandgap of the window layer can be maximized, or both, to increase the transmittance of the window layer for certain wavelengths of optical radiation and thus the responsiveness of photodiode to the certain wavelengths of optical radiation. For example, in one implementation, the photodiode can be an InGaAs photodiode with the window layer having a composition of InAlAs and a relatively thin thickness; this implementation can notably result in a high transmittance of optical radiation both in the near-infrared wavelengths and visible wavelengths.

The photodiode of the preceding paragraph can be used, for example, as a detector in a non-invasive sensor. In addition, advantageously, the photodiode of the preceding paragraph can enable a non-invasive sensor to be constructed which has fewer detectors because the photodiode may serve to detect optical radiation at wavelengths traditionally detected using two or more separate detectors. For example, when the photodiode may be an enhanced InGaAs photodiode, as described herein, with a window layer having a InAlAs composition and a relatively thin thickness, the photodiode can enable the non-invasive sensor to detect optical radiation traditionally detected using one Si photodiode and one traditional InGaAs photodiode with a window layer having a InP composition and a relatively thicker thickness of about 500 nm. As a result, the non-invasive sensor constructed in accordance with the teachings of this disclosure may include fewer detectors or the size of one or more of the detectors can be increased so that the one or more detectors provide greater signal strength. In one example, the surface area covered by the enhanced InGaAs photodiode within the non-invasive sensor can be doubled because the Si photodiode may not be included within the non-invasive sensor, thereby allowing the signal strength of a detector signal output by the enhanced InGaAs photodiode to be doubled over that of the traditional InGaAs photodiode when combined with the Si photodiode.

As used herein, optical radiation at visible wavelengths, in addition to having its ordinary meaning, can refer to optical radiation in the visible spectrum ranging from about 380 nm to about 750 nm. Additionally, as used herein, optical radiation at near-infrared wavelengths, in addition to having its ordinary meaning, can refer to optical radiation in the near-infrared spectrum ranging from about 750 nm to about 1700 nm.

For purposes of summarizing the disclosure, certain aspects, advantages and novel features have been described herein. It is to be understood that not necessarily all such advantages can be achieved in accordance with any particular embodiment. Thus, the embodiments can be embodied or carried out in a manner that achieves or optimizes one advantage or group of advantages as taught herein without necessarily achieving other advantages as can be taught or suggested herein.

II. Patient Monitoring System with Non-Invasive Sensor

Figure 1:
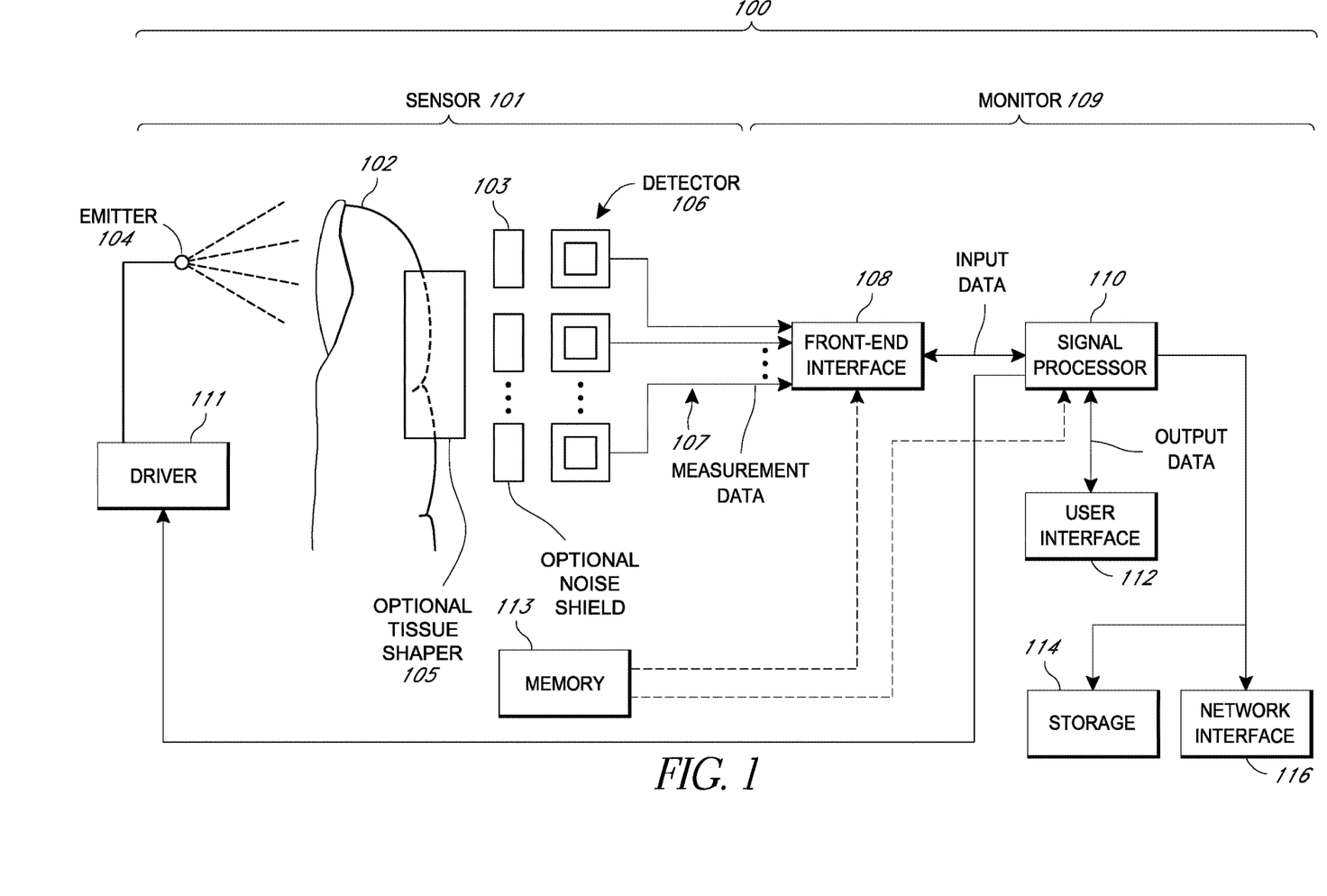
FIG. 1 illustrates a block diagram of an example data collection system capable of non-invasively measuring one or more analytes of a patient.

FIG. 1 illustrates an example of a data collection system 100. The data collection system 100 non-invasively can measure a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. The data collection system 100 can also measure additional blood analytes or other physiological parameters useful in determining a state or trend of wellness of a patient.

The data collection system 100 can measure analyte concentrations, including glucose, at least in part by detecting optical radiation attenuated by a measurement site 102. The measurement site 102 can be any location on a patient's body, such as a finger, foot, ear lobe, or the like. For convenience, this disclosure is described primarily in the context of a finger measurement site 102. However, the features of the embodiments disclosed herein can be used with other measurement sites 102.

In the depicted embodiment, the data collection system 100 includes an optional tissue thickness adjuster or tissue shaper 105, which can include one or more protrusions, bumps, lenses, or other suitable tissue-shaping mechanisms. In certain embodiments, the tissue shaper 105 is a flat or substantially flat surface that can be positioned proximate the measurement site 102 and that can apply sufficient pressure to cause the tissue of the measurement site 102 to be flat or substantially flat. In other embodiments, the tissue shaper 105 is a convex or substantially convex surface with respect to the measurement site 102.

The data collection system 100 shown also includes an optional noise shield 103. The noise shield 103 can be adapted to reduce electromagnetic noise while increasing the transmittance of optical radiation from the measurement site 102 to one or more detectors 106. For example, the noise shield 103 can advantageously include a conductive coated glass or metal grid electrically communicating with one or more other shields of the sensor 101 or electrically grounded.

The measurement site 102 can be located somewhere along a non-dominant arm or a non-dominant hand, e.g., a right-handed person's left arm or left hand. In some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection system 100 can be used on a person's non-dominant hand or arm.

The data collection system 100 can include a sensor 101 (or multiple sensors) that is coupled to a processing device or physiological monitor 109. In some implementations, the sensor 101 and the monitor 109 can be integrated together into a single unit. In other implementations, the sensor 101 and the monitor 109 can be separate from each other and communicate one with another in any suitable manner, such as via a wired or wireless connection. The sensor 101 and monitor 109 can be attachable and detachable from each other for the convenience of the user or caregiver, for ease of storage, sterility issues, or the like. The sensor 101 and the monitor 109 will now be further described.

In the depicted embodiment shown in FIG. 1, the sensor 101 includes an emitter 104, a set of detectors 106, and a front-end interface 108. The emitter 104 can serve as the source of optical radiation transmitted towards the measurement site 102. The emitter 104 can include one or more sources of optical radiation, such as light-emitting diodes (LEDs), laser diodes, incandescent bulbs with appropriate frequency-selective filters, combinations of the same, or the like. In an embodiment, the emitter 104 includes sets of optical sources that are capable of emitting visible and near-infrared optical radiation.

In some embodiments, the emitter 104 is used as a point optical source, and thus, the one or more optical sources of the emitter 104 can be located within a close distance to each other, such as within about a 2 mm to about 4 mm. The emitter 104 can be arranged in an array, such as is described in U.S. Patent Application Publication No. 2006/0211924, filed Sep. 21, 2006, titled "Multiple Wavelength Sensor Emitters," the disclosure of which is hereby incorporated by reference in its entirety. In particular, the emitter 104 can be arranged at least in part as described in paragraphs [0061] through [0068] of the aforementioned publication, which paragraphs are hereby incorporated specifically by reference. Other relative spatial relationships can be used to arrange the emitter 104.

The emitter 104 of the data collection system 100 can emit, for example, combinations of optical radiation in various bands of interest. For instance, for analytes like glucose, the emitter 104 can emit optical radiation at three (3) or more wavelengths between about 1600 nm to about 1700 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes or to distinguish other types of tissue, fluids, tissue properties, fluid properties, combinations of the same or the like.

The emitter 104 can emit optical radiation across other spectra for other analytes. In particular, the emitter 104 can employ optical radiation wavelengths to measure various blood analytes or percentages (e.g., saturation) thereof. For instance, the emitter 104 can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitter 104 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitter 104 can transmit any of a variety of wavelengths of visible or near-infrared optical radiation.

The data collection system 100 also includes a driver 111 that drives the emitter 104. The driver 111 can be a circuit or the like that is controlled by the monitor 109. For example, the driver 111 can provide pulses of current to the emitter 104. In an embodiment, the driver 111 drives the emitter 104 in a progressive fashion, such as in an alternating manner. The driver 111 can drive the emitter 104 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The detectors 106 can capture and measure optical radiation from the measurement site 102. For example, the detectors 106 can capture and measure optical radiation transmitted from the emitter 104 that has been attenuated or reflected from the tissue in the measurement site 102. The detectors 106 can output a detector signal 107 responsive to the optical radiation captured or measured. The detectors 106 can be implemented using one or more photodiodes, phototransistors, or the like. Although the detectors 106 may be described as multiple detectors, in certain embodiments, the detectors 106 instead can be a single detector.

Figure 3:
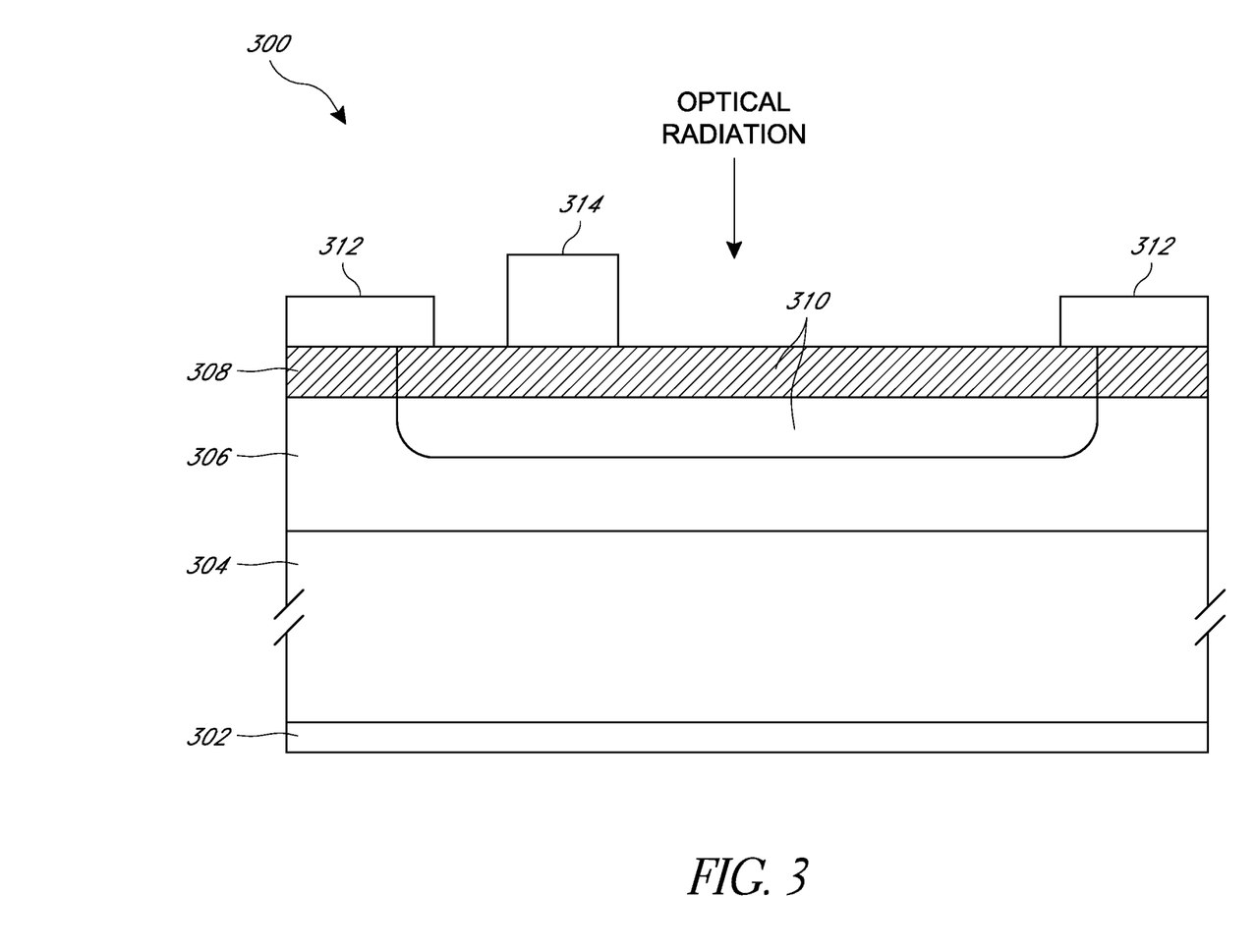
FIG. 3 illustrates an example schematic diagram of a semiconductor device.

In one implementation, the detectors 106 can include one or more photodiodes, such as at least one of the photodiodes described with respect to FIG. 3. The photodiode can detect optical radiation at both visible and near-infrared wavelengths and generate one or more detector signals responsive to the detected optical radiation. The one or more detector signals can have a signal strength sufficient for the detector signal to be usable to determine measurement values for one or more physiological parameters of the patient from the optical radiation detected by the photodiode at both the visible and near-infrared wavelengths. For example, the photodiode can detect optical radiation having a wavelength of about 660 nm in the visible portion of the electromagnetic spectrum and optical radiation having a wavelength of about 1000 nm in the near-infrared portion of the electromagnetic spectrum and generate a detector signal based thereon.

One or more photodiodes of the detectors 106 can be defined in terms of area. In an embodiment, the area of one photodiode can be from about 1 $mm^2$-5 $mm^2$ (or higher) and capable of generating about 100 nanoamps (nA) or less of current resulting from measured optical radiation at full scale. In addition to having its ordinary meaning, the phrase "at full scale" can mean optical radiation saturation of a photodiode amplifier (not shown). The data collection system 100 can, for instance, measure from one photodiode an output current range of approximately about 2 nA to about 100 nA or more full scale. Various other sizes and types of photodiodes can be used with the embodiments of the present disclosure.

The detectors 106 can be arranged with different spatial configurations, such as to provide or not provide a variation of path lengths among at least some of the detectors 106. Some of the detectors 106 can have substantially, or from the perspective of the processing algorithm, effectively, the same path length from the emitter 104. In one example, the detectors 106 can be arranged as is described in U.S. Patent Application Publication No. 2010/0026995, filed Aug. 3, 2009, titled "Multi-stream Sensor for Noninvasive Measurement of Blood Constituents," the disclosure of which is hereby incorporated by reference in its entirety. In particular, the detectors can be arranged at least in part as described with respect to FIGS. 3E and 12A-12H of the aforementioned publication, the associated paragraphs and figures of which are hereby incorporated specifically by reference.

The front-end interface 108 provides an interface that adapts the output of the detectors 106, which is responsive to desired physiological parameters. For example, the front-end interface 108 can adapt a signal 107 received from one or more of the detectors 106 into a form that can be processed by the monitor 109, for example, by a signal processor 110 in the monitor 109. The front-end interface 108 can also amplify current from the detectors 106 at desired signal-to-noise ratios (SNRs), such as to a SNR about 80 decibels (dB), 100 dB, or 120 dB in order to measure various desired analytes. The front-end interface 108 can have its components assembled in the sensor 101, in the monitor 109, in connecting cabling (if used), combinations of the same, or the like. The location of the front-end interface 108 can be chosen based on various factors including space desired for components, desired noise reductions or limits, desired heat reductions or limits, and the like.

The front-end interface 108 can be coupled to the detectors 106 and to the signal processor 110 using a bus, wire, electrical or optical cable, flex circuit, or some other form of signal connection. The front-end interface 108 can also be at least partially integrated with various components, such as the detectors 106. For example, the front-end interface 108 can include one or more integrated circuits that are on the same circuit board as the detectors 106. Other configurations can also be used.

The front-end interface 108 can be implemented using one or more amplifiers, such as transimpedance amplifiers, that are coupled to one or more analog to digital converters (ADCs) (which can be in the monitor 109), such as a sigma-delta ADC. A transimpedance-based front-end interface 108 can employ single-ended circuitry, differential circuitry, or a hybrid configuration. A transimpedance-based front-end interface 108 can be useful for its sampling rate capability and freedom in modulation/demodulation algorithms. For example, this type of front-end interface 108 can advantageously facilitate the sampling of the ADCs being synchronized with the pulses emitted from the emitter 104.

The ADC or ADCs can provide one or more outputs into multiple channels of digital information for processing by the signal processor 110 of the monitor 109. Each channel can correspond to a signal output from a detector 106.

As shown in FIG. 1, the monitor 109 can include the signal processor 110 and a user interface 112, such as a display. The monitor 109 can also include optional outputs alone or in combination with the user interface 112, such as a storage device 114 and a network interface 116. The signal processor 110 can include processing logic that determines measurements for desired analytes, such as glucose, based on the signals received from the detectors 106. The signal processor 110 can be implemented using one or more microprocessors or subprocessors (e.g., cores), digital signal processors, application specific integrated circuits (ASICs), field programmable gate arrays (FPGAs), combinations of the same, and the like.

The signal processor 110 can provide various signals that control the operation of the sensor 101. For example, the signal processor 110 can provide an emitter control signal to the driver 111. This control signal can be useful in order to synchronize, minimize, or reduce jitter in the timing of pulses emitted from the emitter 104. Accordingly, this control signal can be useful in order to cause optical radiation pulses emitted from the emitter 104 to follow a precise timing and consistent pattern. As also shown, an optional memory 113 can be included in the front-end interface 108 or in the signal processor 110. This memory 113 can serve as a buffer or storage location for the front-end interface 108 or the signal processor 110, among other uses.

The user interface 112 can provide an output, for example, on a display, for presentation to a user of the data collection system 100. The user interface 112 can be implemented as a touch-screen display, an LCD display, an organic LED display, or the like. In addition, the user interface 112 can be manipulated to allow for measurement on the non-dominant side of patient. For example, the user interface 112 can include a flip screen, a screen that can be moved from one side to another on the monitor 109, or can include an ability to reorient its display indicia responsive to user input or device orientation. In alternative embodiments, the data collection system 100 can be provided without a user interface 112 and can simply provide an output signal to a separate display or system.

A storage device 114 and a network interface 116 represent other optional output connections that can be included in the monitor 109. The storage device 114 can include any computer-readable medium, such as a memory device, hard disk storage, EEPROM, flash drive, or the like. The various software or firmware applications can be stored in the storage device 114, which can be executed by the signal processor 110 or another processor of the monitor 109. The network interface 116 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 109 to communicate and share data with other devices. The monitor 109 can also include various other components not shown, such as a microprocessor, graphics processor, or controller to output the user interface 112, to control data communications, to compute data trending, or to perform other operations.

Although not shown in the depicted embodiment, the data collection system 100 can include various other components or can be configured in different ways. For example, the sensor 101 can have both the emitter 104 and detectors 106 on the same side of the measurement site 102 and use reflectance to measure analytes. The data collection system 100 can also include a sensor that measures the power of optical radiation emitted from the emitter 104. Moreover, although the detectors 106 may be initially constructed to include one of the photodiodes described with respect to FIG. 3, the detectors 106 may also instead be retrofitted with one of the photodiodes described with respect to FIG. 3 in some implementations.

Figure 2:
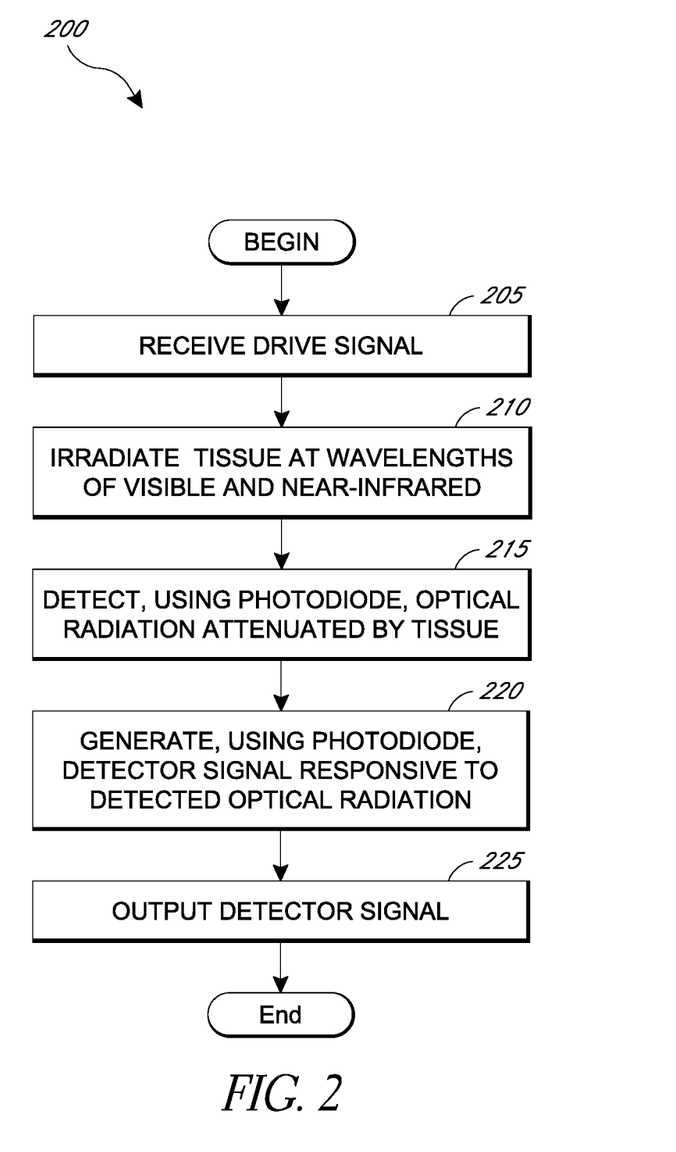
FIG. 2 illustrates an example sensor operation process.

FIG. 2 illustrates an example sensor operation process 200. The process 200 illustrates an example operation of the sensor 101 and may be implemented by the various components shown in the data collection system 100. For convenience, the process 200 is described in the context of the data collection system 100 but may instead be implemented by other systems described herein or other sensor systems not shown. The process 200 provides one example approach by which the sensor 101 can emit visible and near-infrared optical radiation wavelengths and detect with a photodiode, such as one of the photodiodes described with respect to FIG. 3, the optical radiation after attenuation by tissue of a patient. Advantageously, in certain embodiments, the process 200 enables the sensor 101 to output from the photodiode a detector signal responsive to both visible and near-infrared wavelengths after attenuation by the tissue.

At block 205, the emitter 104 can receive a drive signal from the driver 111. At block 210, the drive signal can cause the emitter 104 to irradiate tissue of a patient at wavelengths of visible optical radiation and near-infrared optical radiation. At block 215, a photodiode of the detectors 106 can detect the optical radiation after attenuation by the tissue. At block 220, the photodiode of the detectors 106 can generate one or more detector signals responsive to the detected optical radiation at the visible and near-infrared wavelengths. For instance, the photodiode can generate one signal responsive to the detected optical radiation at the visible wavelength and another signal responsive to the detected optical radiation at the near-infrared wavelength when the visible and near-infrared wavelengths are emitted at different times, or the photodiode can output can output a combined signal responsive to the detected optical radiation at the visible and near-infrared wavelengths when the visible and near-infrared wavelengths are emitted at substantially the same time. At block 225, the sensor 101 can output the one or more detector signals for processing by the signal processor 110 to determine measurement values for one or more physiological parameters of the patient.

III. Example Photodiodes

FIG. 3 illustrates an example schematic diagram of a semiconductor device 300. The semiconductor device 300 can, for instance, be part of an integrated semiconductor structure including one or more other components. The semiconductor device 300 includes a distal side metal contact 302 and a proximal side metal contact 314. The semiconductor device 300 further includes a semiconductor wafer 304, an absorption region 306, a detector window layer 308, a diffusion region 310, and a diffusion mask 312 that together can form a photodiode, such as a photodiode usable as one of the detectors 106 of FIG. 1. Optical radiation can enter the photodiode through the detector window layer 308 before passing to other layers of the photodiode, such as the absorption region 306. Although not illustrated, an anti-reflective coating can be applied to the surface of the photodiode, such as the detector window layer 308, to increase the transmittance of the photodiode.

In one implementation, the distal side metal contact 302 can be an n-type region contact and the proximal side metal contact 314 can be a p-type region contact. The semiconductor wafer 304 can, for instance, be an n-type InP wafer, which includes indium and phosphorous. The absorption region 306 can, for instance, be (i) an n-type or undoped InGaAs absorption region, which includes indium, gallium, and arsenic, (ii) an n-type or undoped InAlGaAs absorption region, which includes indium, aluminum, gallium, and arsenic, or (iii) an n-type or undoped InGaAsP region, which includes indium, gallium, arsenic, and phosphorous. The diffusion region 310 can, for instance, be a diffused region that turns n-type or undoped material into a p-type region to form a p-n semiconductor junction in selected areas defined by the diffusion mask 312. The diffusion mask 312 can, for instance, be a SiN or $SiO_2$ diffusion mask. The photodiode, in one implementation, can accordingly be an InGaAs PIN photodiode.

The detector window layer 308 can be a layer that is sufficiently thin so that the detector window layer 308 passes visible optical radiation for detection by the photodiode and yet provides passivation of the absorption region 306 and the diffusion region 310, which can be a zinc-diffused P region, so that electron-hole pairs generated by the visible optical radiation, including short-wavelength optical radiation, near the surface of the photodiode (for example, in the P-region) have a lower recombination rate resulting in a quantum efficiency enhancement at visible wavelengths. For example, the detector window layer 308 can be a layer having a thickness of less than about 150 nm, such as a thickness ranging from about 25 nm to about 150 nm, from about 40 nm to about 130 nm, from about 50 nm to about 100 nm, or from about 45 nm to about 55 nm or a thickness of about 50 nm. Because the detector window layer 308 being thinner may result in more visible wavelengths passing into the photodiode, the detector window layer 308 can be desirably about 50 nm in certain implementations. The detector window layer 308 can be an epitaxially grown layer.

In one example, the detector window layer 308 can be an InP layer, which includes indium and phosphorous. The InP layer can have a bandgap of about 1.34 eV at 25° C. If the InP layer is about 400 nm thick, the external quantum efficiency at 660 nm can be about 8%. If the InP layer may be made thinner such as around 50 nm, the external quantum efficiency at 660 nm can be about 58%. Thinner layers, such as about window layers having a thickness of about 25 nm, can be made, but if made too thin, the microfabrication procedures used to make the photodiode may, in some instances, slightly etch or oxide the window layers, leaving no or minimal window layer so that the surface of the InGaAs or InAlGaAs photodiode may be unpassivated and have a lower quantum efficiency for visible wavelengths (for example, shorter wavelengths) due to enhanced recombination of photogenerated carriers in the layer at the unpassivated surface. There can thus exist an optimum InP layer thickness between 0 nm and about 50 nm for such devices, in particular implementations.

As another example, the detector window layer 308 can be an InAlAs layer, which includes indium, aluminum, and arsenic, which can either be of a composition whose atomic crystal lattice constant is lattice-matched or lattice mismatched to the absorption region 306 and semiconductor wafer 304. Advantageously, in certain embodiments, the InAlAs layer can be desirably thin to efficiently pass visible optical radiation for detection by the photodiode, similar to the InP layer example explained in the preceding paragraph. In one implementation, the InAlAs layer can be formed of a composition of $In_{0.52}Al_{0.48}As$ that has a bandgap of about 1.52 eV at 25° C. and is lattice-matched to the semiconductor wafer 304. It has been determined that the $In_{0.52}Al_{0.48}As$ layer can begin to strongly attenuate optical radiation at wavelengths shorter than about 817 nm as compared to an attenuation wavelength of about 920 nm at 25° C. for an InP layer and therefore can result in a relatively higher external quantum efficiency. In another implementation, the InAlAs layer can be formed of a composition of $In_{0.46}Al_{0.54}As$ that has a larger bandgap of about 1.68 eV and is not lattice-matched to the semiconductor wafer 304. It has been determined that the $In_{0.46}Al_{0.54}As$ layer can begin to strongly attenuate optical radiation at wavelengths shorter than about 739 nm and the external quantum efficiency for the photodiode with the $In_{0.46}Al_{0.54}As$ layer may be about 78% at a wavelength about 660 nm. Because the detector window layer 308 having a higher bandgap can result in more visible optical radiation passing into the photodiode, the detector window layer 308 can be desirably composed of $In_{0.46}Al_{0.54}As$ in certain implementations. Although the InAlAs composition may be lattice-mismatched to the crystal lattice constant of one or more of the underlying layers, is the layer can be generally sufficiently thin so that the layer may be strained to fit on the underlying crystal lattice without generation of dislocation defects, a condition that can be known as pseudomorphic growth. The following Table 1 summarizes some measured data for the above-referenced window layers of a similar photodiode structure and compares them to a model result for a photodiode structure with a window layer composed of InP with a thickness of 400 nm.

TABLE 1

| Layer Composition | Thickness | Bandgap | Lattice-Matched | External Quantum Efficiency at 660 nm Wavelength |
|---|---|---|---|---|
| InP | 400 nm | 1.34 eV | Yes | 8% |
| InP | 50 nm | 1.34 eV | Yes | 58% |
| $In_{0.46}Al_{0.54}As$ | 50 nm | 1.68 eV | No | 78% |

Figure 4:
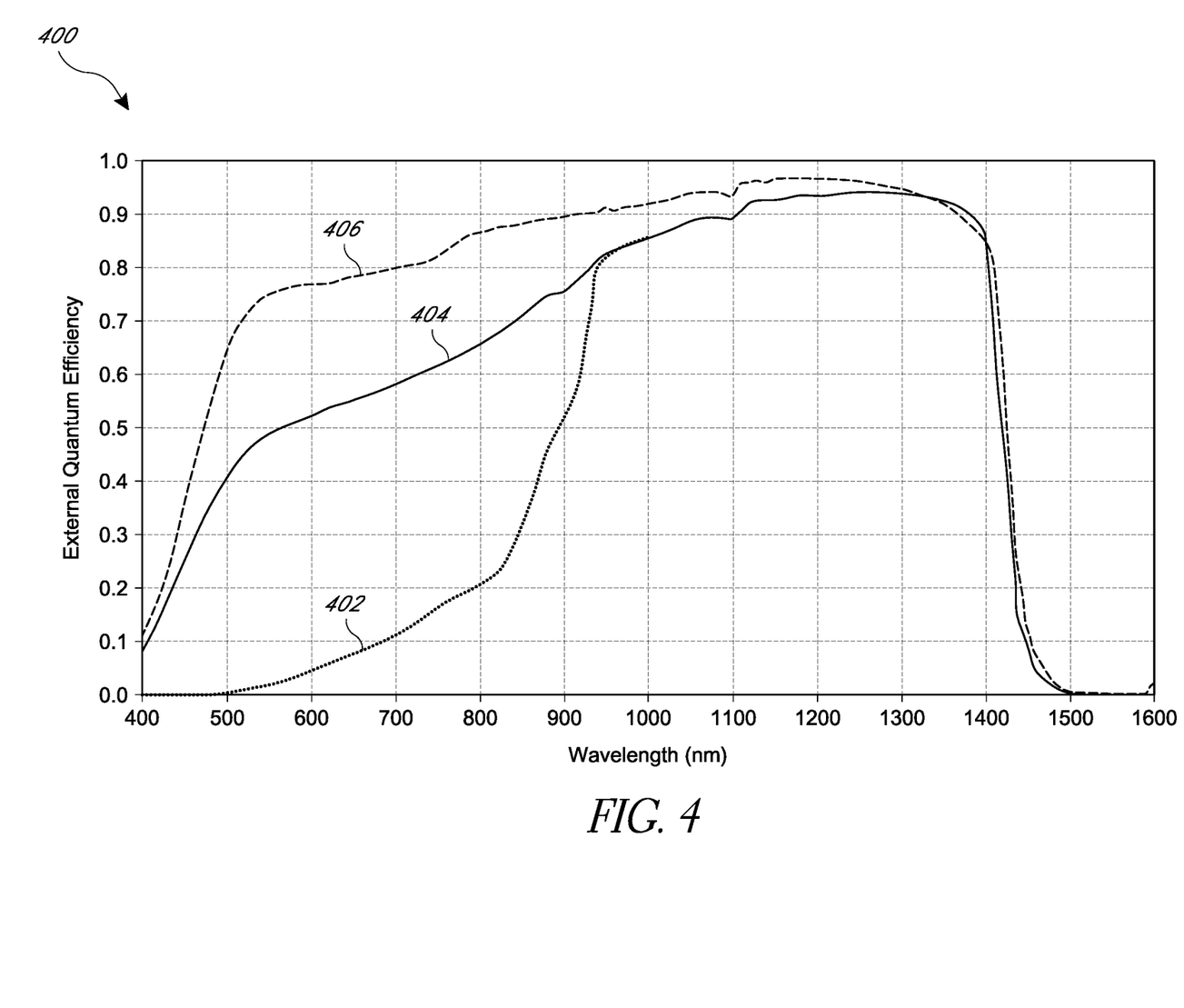
FIG. 4 illustrates a graph of quantum efficiency versus optical radiation wavelength for various example photodiodes.

FIG. 4 illustrates a graph 400 of quantum efficiency versus optical radiation wavelength for various example photodiodes. The graph 400 illustrates that the teachings of this disclosure can enable the construction of a photodiode that has a relatively higher quantum efficiency at both visible and near-infrared wavelengths compared to a traditional photodiode. As used herein, external quantum efficiency, in addition to having its ordinary meaning, can refer to the ratio of the number of charge carriers collected to the number of photons of a given energy shining on the photodiode from outside the photodiode. The external quantum efficiency, for instance, can be proportional to the amount of current that a photodiode produces when irradiated by photons of a particular wavelength.

The curve 402 depicts a model relationship between external quantum efficiency versus optical radiation wavelength for a traditional photodiode formed from the semiconductor device 300 where the absorption region 306 is an n-type InAlGaAs absorption region and the detector window layer 308 has a thickness of about 400 nm and is an InP layer. The curve 404 depicts the measured relationship between external quantum efficiency versus optical radiation wavelength for a photodiode formed from the semiconductor device 300 where the absorption region 306 is an n-type InAlGaAs absorption region and the detector window layer 308 has a thickness of about 50 nm and is an InP layer. The curve 406 depicts the measured relationship between external quantum efficiency versus optical radiation wavelength for a photodiode formed from the semiconductor device 300 where the absorption region 306 is an n-type InAlGaAs absorption region and the detector window layer 308 has a thickness of about 50 nm and is a lattice-mismatched $In_{0.46}Al_{0.54}As$ layer.

As can be seen from curves 404 and 406 of the graph 400, the quantum efficiency of an enhanced photodiode constructed in accordance with teachings of this disclosure can notably have an external quantum efficiency of greater than about 30% (such as an external quantum efficiency ranging from about 30% to about 90%, from about 50% to about 85%, or from about 60% to about 80% or an external quantum efficiency of about 50%, about 60%, about 70%, about 80% or about 90%) at wavelengths ranging from about 450 nm to 850 nm. Such an enhanced photodiode can accordingly be used, for instance, to detect optical radiation at wavelengths ranging from about 450 nm to about 850 nm, as well as from about 850 nm to about 1400 nm or 1430 nm.

Although the curves 402, 404, and 406 depict the quantum efficiency versus optical radiation wavelength for a photodiode where the absorption region 306 is an n-type InAlGaAs absorption region, the absorption region 306 may in some cases instead be an n-type InGaAs absorption region as mentioned previously. If the curves 402, 404, and 406 were depicted for photodiodes including the n-type InGaAs absorption region, the responsiveness of the photodiodes would further extend to about 1700 nm rather than about 1430 nm as illustrated in the graph 400. Therefore, in such implementations, an enhanced photodiode can be used, for instance, to detect optical radiation at wavelengths ranging from about 450 nm to about 850 nm, as well as from about 850 nm to about 1700 nm. In such implementations, the enhanced photodiode can, for instance, have an external quantum efficiency of greater than about 70% (such as an external quantum efficiency ranging from about 70% to about 95%, from about 80% to about 95%, from about 85% to about 95%, or from about 90% to about 95% or an external quantum efficiency of about 70%, about 80%, about 85%, about 90%, or about 95%) at wavelengths ranging from about 1400 nm to 1700 nm.

As illustrated by the graph 400, an enhanced photodiode having the performance characteristics of the curve 404 can have an external quantum efficiency of about 9% at 400 nm, 28% at 450 nm, 41% at 500 nm, 49% at 550 nm, 52% at 600 nm, 55% at 650 nm, 58% at 700 nm, 62% at 750 nm, 65% at 800 nm, 71% at 850 nm, 75% at 900 nm, 82% at 950 nm, 85% at 1000 nm, 89% at 1050 nm, 89% at 1100 nm, 92% at 1150 nm, 92% at 1200 nm, 92% at 1250 nm, 92% at 1300 nm, 92% at 1350 nm, 85% at 1400 nm, and 5% at 1450 nm. In addition, as illustrated by the graph 400, an enhanced photodiode having the performance characteristics of the curve 406 can have an external quantum efficiency of about 12% at 400 nm, 40% at 450 nm, 65% at 500 nm, 75% at 550 nm, 77% at 600 nm, 78% at 650 nm, 80% at 700 nm, 82% at 750 nm, 86% at 800 nm, 88% at 850 nm, 90% at 900 nm, 91% at 950 nm, 92% at 1000 nm, 94% at 1050 nm, 93% at 1100 nm, 96% at 1150 nm, 96% at 1200 nm, 95% at 1250 nm, 94% at 1300 nm, 92% at 1350 nm, 85% at 1400 nm, and 10% at 1450 nm. Moreover, an enhanced photodiode constructed in accordance with the teachings of this disclosure can thus have an external quantum efficiency of at least the external quantum efficiency of the curve 404 or the curve 406 at the various wavelengths illustrated in FIG. 4, as well as at the additional range of wavelengths from about 1400 nm to 1700 nm as described herein. Furthermore, an enhanced photodiode constructed in accordance with the teachings of this disclosure can thus have an external quantum efficiency of at least 10% to 30% (for example, 10%, 15%, 20%, 25%, or 30%) at wavelengths ranging from 450 nm to 1400 nm, at least 10% to 65% (for example, 10%, 15%, 20%, 25%, 30%, 35%, 40%, 45%, 50%, 55%, 60%, or 65%) at wavelengths ranging from 500 nm to 1400 nm, at least 10% to 75% (for example, 10%, 15%, 20%, 25%, 30%, 35%, 40%, 45%, 50%, 55%, 60%, 65%, 70%, or 75%) at wavelengths ranging from 550 nm to 1400 nm, at least 10% to 75% (for example, 10%, 15%, 20%, 25%, 30%, 35%, 40%, 45%, 50%, 55%, 60%, 65%, 70%, or 75%) at wavelengths ranging from 600 nm to 1400 nm, at least 10% to 78% (for example, 10%, 15%, 20%, 25%, 30%, 35%, 40%, 45%, 50%, 55%, 60%, 65%, 70%, 75%, or 78%) at wavelengths ranging from 650 nm to 1400 nm, at least 15% to 80% (for example, 15%, 20%, 25%, 30%, 35%, 40%, 45%, 50%, 55%, 60%, 65%, 70%, 75%, or 80%) at wavelengths ranging from 700 nm to 1400 nm, at least 20% to 80% (for example, 20%, 25%, 30%, 35%, 40%, 45%, 50%, 55%, 60%, 65%, 70%, 75%, or 80%) at wavelengths ranging from 750 nm to 1400 nm, at least 25% to 85% (for example, 25%, 30%, 35%, 40%, 45%, 50%, 55%, 60%, 65%, 70%, 75%, 80%, or 85%) at wavelengths ranging from 800 nm to 1400 nm, at least 30% to 85% (for example, 30%, 35%, 40%, 45%, 50%, 55%, 60%, 65%, 70%, 75%, 80%, or 85%) at wavelengths ranging from 850 nm to 1400 nm, at least 55% to 85% (for example, 55%, 60%, 65%, 70%, 75%, 80%, or 85%) at wavelengths ranging from 900 nm to 1400 nm, at least 85% at wavelengths ranging from 950 nm to 1400 nm, or at least 90% at wavelengths ranging from 900 nm to 1350 nm.

As illustrated by the graph 400, an enhanced photodiode constructed in accordance with the teachings of this disclosure can have an external quantum efficiency ranging at least from about 9% to 12% at 400 nm, 28% to 40% at 450 nm, 41% to 65% at 500 nm, 49% to 75% at 550 nm, 52% to 77% at 600 nm, 55% to 78% at 650 nm, 58% to 80% at 700 nm, 62% to 82% at 750 nm, 65% to 86% at 800 nm, 71% to 88% at 850 nm, 75% to 90% at 900 nm, 82% to 91% at 950 nm, 85% to 92% at 1000 nm, 89% to 94% at 1050 nm, 89% to 93% at 1100 nm, 92% to 96% at 1150 nm, 92% to 96% at 1200 nm, 92% to 95% at 1250 nm, 92% to 94% at 1300 nm, 92% to 92% at 1350 nm, 85% to 85% at 1400 nm, and 5% to 10% at 1450 nm.

In some embodiments, when a photodiode has an external quantum efficiency at a particular wavelength that is below a threshold quantum efficiency level, an output current generated by the photodiode when irradiated by photons of the particular wavelength can be sufficiently low such that the photodiode may be considered to not detect the particular wavelength. This can, in some instances, be because the output current generated by the photodiode when irradiated by photons of the particular wavelength may be insufficient for use in confidently determining that the photodiode detected the particular wavelength. The threshold quantum efficiency level can vary, in certain embodiments, based at least on a system design in which the photodiode is used. For example, in certain medical device applications, such as in some example non-invasive sensor detector applications, the threshold quantum efficiency level can be about 30%, about 25%, about 20%, about 15%, or about 10%, such that when a photodiode detects particular wavelengths for which the photodiode has an external quantum efficiency below the threshold quantum efficiency level, the output current provided by the photodiode may be insufficient for the non-invasive sensor to confidently determine that the photodiode detected the particular wavelengths. Accordingly, in some instances, the photodiode may not be used to detect wavelengths for which the photodiode has an external quantum efficiency below the threshold quantum efficiency level, or the output current from the photodiode may be discarded as not providing usable information or information of sufficient quality if the output current is below a threshold current corresponding to the threshold quantum efficiency level.

Moreover, although some applications of the photodiode of the semiconductor device 300 are described in the context of a non-invasive sensor, the photodiode can be useful in numerous other applications. For example, the photodiode can be part of a spectrometer in industrial or manufacturing applications (for instance, in applications related to plastics, petroleum, chemical, or the like) and used to detect a broad range of electromagnetic radiation for detecting a spectrum of electromagnetic radiation. As another example, the photodiode can be part of a non-contact temperature measurement system and used to detect a broad range of electromagnetic radiation to determine a detected temperature. As a further example, the photodiode can be part of a flame monitoring or control system and used to detect one or more characteristics of a flame from the detected broad spectrum of electromagnetic radiation. Moreover, the photodiode can be part of a diode laser monitoring system (for instance, for telecommunications or lidar applications) and used to detect a broad range of electromagnetic radiation from one or more lasers.

IV. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Terms such as "substantially," "about," "approximately" or the like as used in referring to a relationship between two objects is intended to reflect not only an exact relationship but also variances in that relationship that may be due to various factors such as the effects of environmental conditions, common error tolerances, manufacturing variances, or the like. It should further be understood that although some values or other relationships may be expressed herein without a modifier, these values or other relationships may also be exact or may include a degree of variation due to various factors such as the effects of environmental conditions, common error tolerances, or the like. For example, when referring to wavelengths of electromagnetic radiation, about a specified wavelength can, in some contexts, refer to a wavelength variation of around less than 1% (such as a variation of 1%, 0.8%, 0.5%, or 0.3%) from the specified wavelength. Accordingly, an about 660 nm wavelength can refer to 660 nm±6 nm, 660 nm±5 nm, 660 nm±3 nm, or 660 nm±2 nm. As another example, when referring to a thickness of a layer, about a specified thickness can, in some contexts, refer to a thickness variation of around less than 5% (such as a variation of 5%, 3%, 2%, 1%, or 0.1%) from the specified thickness. Accordingly, an about 50 nm thickness can refer to 50 nm±2.5 nm, 50 nm±1.5 nm, 50 nm±1 nm, or 50 nm±0.5 nm, or 50 nm±0.05 nm. As a further example, when referring to an eV of a bandgap, about a specified eV can, in some contexts, refer to an eV variation of around less than 2% (such as a variation of 2%, 1.5%, 1%, or 0.5%) from the specified eV. Accordingly, an about 1.52 eV bandgap can refer to 1.52 eV±0.03 eV, 1.52 eV±0.023 eV, 1.52 eV±0.015 eV, or 1.52 eV±0.008 eV. In another example, when referring to an external quantum efficiency of a layer, about a specified external quantum efficiency percentage can, in some contexts, refer to an external quantum efficiency percentage variation of around less than 3% (such as a variation of 3%, 2%, 1%, or 0.5%) from the specified external quantum efficiency percentage. Accordingly, an about 58% external quantum efficiency can refer to 58%±3%, 58%±2%, 58%±1%, or 58%±0.5%.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed:

1. A physiological sensor for measuring physiological parameters of a monitored patient, the physiological sensor comprising:
   a sensor housing;
   an emitter configured to emit optical radiation at one or more wavelengths; and
   one or more detectors configured to be positioned proximate to the emitter and tissue of a patient by the sensor housing, the one or more detectors comprising a semiconductor device configured to detect the optical radiation after attenuation by the tissue and generate a detector signal responsive to the detected optical radiation,
   wherein the semiconductor device comprises a window layer, a diffusion region, an absorption region, and a semiconductor wafer, the absorption region being between the window layer and the semiconductor wafer, and
   wherein the window layer has a thickness ranging from about 25 nm to about 150 nm, the diffusion region being a p-type region, the absorption region being an undoped region or a n-type region, the semiconductor wafer being the n-type region.

2. The physiological sensor of claim 1, wherein the absorption region is adjacent to the semiconductor wafer.

3. The physiological sensor of claim 1, wherein the window layer and the diffusion region are configured to receive the optical radiation prior to the absorption region and the semiconductor wafer receiving the optical radiation.

4. The physiological sensor of claim 3, wherein the absorption region is configured to receive the optical radiation prior to the semiconductor wafer receiving the optical radiation.

5. The physiological sensor of claim 1, further comprising:
   a first metal contact adjacent to the semiconductor wafer; and
   a second metal contact adjacent to the window layer.

6. The physiological sensor of claim 5, wherein the first metal contact is the n-type region, and the second metal contact is the p-type region.

7. The physiological sensor of claim 1, wherein the window layer, the diffusion region, the absorption region, and the semiconductor wafer form at least part of a photodiode.

8. The physiological sensor of claim 1, wherein the thickness ranges from about 50 nm to about 100 nm.

9. The physiological sensor of claim 1, wherein the thickness is about 50 nm.

10. The physiological sensor of claim 1, wherein the absorption region comprises indium, gallium, and arsenic, and the window layer comprises indium, aluminum, and arsenic.

11. The physiological sensor of claim 1, wherein the absorption region comprises indium, gallium, and arsenic, and the window layer comprises indium and phosphorus.

12. The physiological sensor of claim 1, wherein the window layer is not lattice matched to the semiconductor wafer.

13. The physiological sensor of claim 1, wherein the window layer is lattice matched to the semiconductor wafer.

14. The physiological sensor of claim 1, further comprising an anti-reflective coating on the window layer.

15. The physiological sensor of claim 1, wherein the diffusion region is part of the window layer and the absorption region.

16. The physiological sensor of claim 1, wherein the window layer is the p-type region.

17. The physiological sensor of claim 1, wherein the semiconductor device has a surface area of at least 5 mm$^2$ over which the semiconductor device is configured to detect the optical radiation after attenuation by the tissue.

18. The physiological sensor of claim 1, wherein the semiconductor device is configured to generate the detector signal to have a current of at least 100 nA.

19. The physiological sensor of claim 1, in combination with a patient monitor configured to determine a measurement value for a physiological parameter from the detector signal.

20. The physiological sensor of claim 19, in combination with the patient monitor, wherein the physiological parameter comprises a blood analyte.

* * * * *